(12) United States Patent
Gujral et al.

(10) Patent No.: US 9,572,766 B2
(45) Date of Patent: Feb. 21, 2017

(54) POLYHERBAL COMPOSITION FOR SKIN CARE

(71) Applicant: Shiromani Gurudwara Prabandhak Committee's Guru Nanak Khalsa College, Mumbai (IN)

(72) Inventors: Sukhjeet Kaur Gujral, Mumbai (IN); Ramesh Trimbak Sane, Mumbai (IN)

(73) Assignee: Shiromani Gurudwara Prabandhak Committee's Guru Nanak Khalsa College, Mumbai (IN)

( * ) Notice: Subject to any disclaimer, the term of this patent is extended or adjusted under 35 U.S.C. 154(b) by 0 days.

(21) Appl. No.: 14/371,106

(22) PCT Filed: Jan. 7, 2013

(86) PCT No.: PCT/IN2013/000009
§ 371 (c)(1),
(2) Date: Jul. 8, 2014

(87) PCT Pub. No.: WO2013/114394
PCT Pub. Date: Aug. 8, 2013

(65) Prior Publication Data
US 2014/0356419 A1    Dec. 4, 2014

(30) Foreign Application Priority Data

Jan. 9, 2012 (IN) .............................. 68/MUM/2012

(51) Int. Cl.
| | | |
|---|---|---|
| *A61K 8/97* | (2006.01) | |
| *A61K 9/51* | (2006.01) | |
| *A61Q 17/04* | (2006.01) | |
| *A61Q 19/08* | (2006.01) | |
| *A61Q 19/00* | (2006.01) | |
| *A61Q 19/02* | (2006.01) | |

(52) U.S. Cl.
CPC ................ *A61K 8/97* (2013.01); *A61Q 19/02* (2013.01); *A61Q 19/08* (2013.01); *A61K 2800/10* (2013.01); *A61K 2800/5922* (2013.01)

(58) Field of Classification Search
CPC .... A61K 2300/00; A61K 9/0014; A61K 8/97; A61K 2039/55555; A61K 36/736; A61K 9/127; A61Q 19/08; A61Q 19/00; A61Q 19/02; A61Q 17/04
See application file for complete search history.

(56) References Cited

U.S. PATENT DOCUMENTS

2011/0086116 A1    4/2011   Florence et al.

FOREIGN PATENT DOCUMENTS

| | | | |
|---|---|---|---|
| CN | 101095934 B | 5/2010 | |
| DE | 29809327 U1 | 7/1999 | |
| FR | EP 1104672 A1 * | 6/2001 | ............. A61K 8/498 |
| FR | 2829694 A1 | 3/2003 | |
| JP | 2292208 A | 12/1990 | |
| JP | 717846 A | 1/1995 | |
| JP | 7126149 A | 5/1995 | |
| JP | 10330222 A | 12/1998 | |
| JP | 1112122 A | 1/1999 | |
| JP | 2003176232 A | 6/2003 | |
| JP | 2011157319 A | 8/2011 | |
| KR | 1020070070659 A | 7/2007 | |

OTHER PUBLICATIONS

Merrriam-Webster's Online Medical Dictionary. Medical Definition of Extract. Apr. 24, 2009. <http://www.merriam-webster.com/medical/extract>.*
Priyavrata Sharma, Priyanighantu, p. 04-08, Ref.pg. No. of publication:19, Ed. 1st 2004, Chaukhamba Surabharti Prakashana, Varanasi, India.
Govinda Dasa, Bhaisajya Ratnavali, (p. 09-15), Ref.pg. No. of publication:666, Edn. 14th, 2001, Chaukhamba Sanskrit Sansthan, Varanasi, India.
Sodhala, Gadanigrahah Part-3 (Salakya-Pancakarma Khanda), p. 16-22, Ref.pg. No. of publication:389, Ed. 3rd 1999, Chaukhamba Sanskrit Sansthan, Varanasi, India.

* cited by examiner

*Primary Examiner* — Frederick Krass
*Assistant Examiner* — Tracy Liu
(74) *Attorney, Agent, or Firm* — The Webb Law Firm

(57) ABSTRACT

Described herein is a polyherbal composition effective in skin care, including singularly or in certain combinations 0.01% to 15% of *Ziziphus* extract, 0.01% to 10% of *Prunus* extract, suitable delivery system, and a suitable carrier.

9 Claims, No Drawings

POLYHERBAL COMPOSITION FOR SKIN CARE

CROSS-REFERENCE TO RELATED APPLICATIONS

This application is the United States national phase of International Application No. PCT/IN2013/000009 filed Jan. 7, 2013, and claims priority to Indian Patent Application No. 68/MUM/2012 filed Jan. 9, 2012, the disclosures of which are hereby incorporated in their entirety by reference.

FIELD OF INVENTION

This invention relates to a polyherbal composition for skin care and more particularly for alleviating cosmetic and dermatological skin conditions, said composition improving the overall skin texture and condition by providing antiaging and antiwrinkle benefits as well as providing skin lightening benefits, involving the use of a synergistic composition comprising severally or in certain combinations extracts of *Ziziphus mauritiana* and *Prunus puddum* in a suitable delivery system designed for enhancing the trans-membrane and/or topical penetration of said active ingredients and a suitable carrier.

BACKGROUND OF THE INVENTION

Skin is one of the largest organs of the human body. While the skin carries out many functions, the most important ones include protection from the environment, helping to control body temperature as well as fluid and electrolyte balance. Skin also contains nerve receptors that allow you to feel sensations such as touch, pain, and pressure.

Although skin has many layers, it can be generally divided into three main parts namely, the outer part (epidermis) which contains skin cells, pigment, and proteins; the middle part (dermis) which contains blood vessels, nerves, hair follicles, and oil glands besides providing nutrients to the epidermis; and the inner layer under the dermis (the subcutaneous layer) which contains sweat glands, some hair follicles, blood vessels, and fat. Each layer also contains connective tissue with collagen fibers to give support and elastin fibers to provide flexibility and strength.

Skin changes are amongst the most visible signs of skin aging. Evidence of increased aging is manifest in the form of wrinkles, sagging of skin, increased pigmentation and development of age spots.

While skin changes are related to environmental factors, genetic makeup, nutrition, and other factors, the greatest single factor, though, is sun exposure. With aging, the epidermis begins to become thinner, even though the number of cell layers remains unchanged. Also, while the number of pigment-containing cells (melanocytes) decreases, the remaining melanocytes tend to increase in size. Aging skin thus appears thinner, more pale, and clear (translucent). Large pigmented spots (called age spots, liver spots, or lentigos) may begin to appear in sun-exposed areas.

Sebaceous glands produce less oil as you age, making it harder to keep the skin moist, resulting in dryness and itchiness. The sweat glands produce less sweat, making it harder to keep cool, and one is at an increased risk of becoming overheated or developing heat stroke. Growths such as skin tags, warts, and other blemishes are more common in older people.

Changes in the connective tissue reduce the skin's strength and elasticity. This condition is referred to as elastosis and is especially pronounced in sun-exposed areas such as the face (solar elastosis). Elastosis produces a leathery, wrinkled, weather-beaten appearance common to labourers, farmers, sailors, and others who spend a large amount of time outdoors.

A skin wrinkle is a fold, ridge or crease in the skin, which typically appears as a result of aging processes such as glycation or, is caused by habitual facial expressions, aging, sun damage, smoking, poor hydration, and various other factors. Changes in the collagen-elastin matrix brought about by aging as well as the action of Matrix Metalloproteinases (MMP) further aggravates this condition, resulting in the development of fine lines and wrinkles (crow's feet) and as aging progresses, more prominent lines at the nasolabial regions of the face.

A number of ingredients and techniques have been tried to address the problem of skin aging. Well known among the various options is the use of Tretinoin, Epidermal Growth factors, Glycosaminoglycans, Dermal fillers, Botox, Collagen injections, etc. Each of these solutions to aging and wrinkles come with their own advantages as well as disadvantages.

Various plants and herbs have also been used in Ayurveda as well as Chinese and Oriental medicine to counter aging. *Ziziphus mauritiana* (*Ziziphus zizyphus*) commonly called jujube (sometimes jujuba), red date, Chinese date, Korean date, or Indian date is a species of *Ziziphus* in the buckthorn family Rhamnaceae, used primarily as a fruiting shade tree. While the fruit is primarily used for edible purposes, there exists certain literature exists which speaks of the anti-aging benefits of the fruit.

*Prunus puddum* (*Prunus cerasoides*, Wild Himalayan cherry) is a deciduous cherry tree found in East Asia. It is of the family Rosaceae and the genus *Prunus*. It grows in the forests from 1200 to 2400 meters above sea level. Heartwood of *Prunus cerasoides* is moderately hard, strong, aromatic, astringent, bitter, acrid, refrigerant, antipyretic and tonic. It is useful in vitiated conditions of pitta, burning sensations, sprains, wounds, ulcers, leprosy and skin discolorations. It has action similar to olive oil and is used in emollient preparations including nourishing creams, skin creams and cold creams.

Various delivery formats have been used to enhance the efficacy and/or penetration of active ingredients into the skin; some of the latest being liposomes and nanoparticles.

SUMMARY OF THE INVENTION

An object of the invention is to propose a polyherbal composition for skin care and more particularly for alleviating cosmetic and dermatological skin conditions, said composition improving the overall skin texture and condition.

Another object of the invention is to provide antiaging benefits.

Yet another object of the invention is to provide anti-wrinkle benefits.

Yet another object of the invention is to provide skin lightening benefits.

Yet another object of the invention is to provide a means of enhancing the trans-membrane and/or topical penetration of active skin benefit ingredients into the skin.

Further objects will be evident through the description of the invention.

This invention relates to a synergistic polyherbal composition effective in improving overall skin texture and condition, more particularly for alleviating cosmetic and dermatological skin conditions by providing antiaging and antiwrinkle benefits as well as providing skin lightening benefits, comprising severally or in certain combinations
   a) said synergistic polyherbal combination
   b) said suitable delivery system
   c) suitable carrier
wherein said synergistic polyherbal combination includes extracts of *Ziziphus mauritiana, Prunus puddum*
wherein said suitable delivery system is a vesicle based delivery system comprising
   a) at least one phospholipid
   b) at least one sterol
wherein said suitable carrier is a physiologically acceptable carrier or diluent.

DETAILED DESCRIPTION OF THE INVENTION

This invention provides a synergistic Polyherbal composition effective in skin care, comprising singularly or in certain combinations
   a) *Ziziphus* extract—0.01% to 15%
   b) *Prunus* extract—0.01% to 10%
   c) Suitable delivery system and
   d) suitable carrier
the combination has a synergistic effect.

Extraction solvents used for preparing the extracts is selected from a group comprising of water, methanol, ethanol, propanol, butanol, glycerol, 1,3-butylene glycol, methyl acetate, ethyl acetate, benzene, hexane, diethyl ether, acetone, dichloromethane, chloroform and a mixture thereof.

Non limiting examples of *Ziziphus* extract include alcoholic extracts, aqueous extracts, ether extracts, chloroform extracts, ethyl acetate extracts, and mixtures thereof.

Non limiting examples of *Prunus* extract include alcoholic extracts, aqueous extracts, ether extracts, chloroform extracts, ethyl acetate extracts, and mixtures thereof.

The *Ziziphus* extract is obtained from *Ziziphus* species including but not limited to *Ziziphus mauritiana*.

The *Prunus* extract is obtained from *Prunus* species including but not limited to *Prunus puddum*.

While concentrations below and above the range indicated can be used, the concentrations below the range may not provide significant benefits while the concentrations above the range may not provide a level of benefit proportional to contents and costs.

Non limiting examples of suitable delivery systems include liposomes, lipid nanoparticles, microemulsions, nanoelulsions, ethosomes.

Standard methodologies commonly used in the field for preparing delivery systems including but not limited to injection method, attrition, pyrolysis, etc. may be adopted in order to prepare the said delivery systems.

Non limiting examples of suitable carriers include water, vegetable oil, mineral oil, creams, lotions, gels and any other dermatologically acceptable carrier. The carrier can itself be inert or possess dermatological benefits of its own.

Non limiting examples of product formats include powder, lotions, gel, spray, stick cream, ointment, liquid, emulsion, aerosol, mask.

The compositions can be easily prepared by any method known in the art, using other additives commonly used in the field for preparing such similar compositions.

Suitable preservative systems commonly used in the field for preparing such similar compositions may be adopted in order to ensure long term stability of the said compositions.

The following examples are illustrations of the invention, but the invention is not limited to the specific illustrations given. It is expected that the person skilled in the relevant art will arrive at other variations, which although differing from the specific examples do not depart from the spirit and scope of the invention as described and claimed herein.

Example 1

| Sr. No. | Ingredient | Percentage |
| --- | --- | --- |
| 1 | *Ziziphus* aq. extract | 3.0% |
| 2 | *Prunus* aq. extract | 2.25% |
| 3 | Phospholipid | 1.72% |
| 4 | Cholesterol | 0.45% |
| 5 | Gel Base | q.s. |

Example 2

| Sr. No. | Ingredient | Percentage |
| --- | --- | --- |
| 1 | *Ziziphus* alc. extract | 0.5% |
| 2 | *Prunus* aq. extract | 0.3% |
| 3 | Phospholipid | 0.84% |
| 4 | Cholesterol | 0.21% |
| 5 | Gel Base | q.s. |

Example 3

| Sr. No. | Ingredient | Percentage |
| --- | --- | --- |
| 1 | *Ziziphus* alc. extract | 8.0% |
| 2 | *Prunus* aq. extract | 4.0% |
| 3 | Phospholipid | 2.15% |
| 4 | Cholesterol | 0.5% |
| 5 | Cream base (water-in-oil) | q.s. |

Example 4

| Sr. No. | Ingredient | Percentage |
| --- | --- | --- |
| 1 | *Ziziphus* (ethyl acetate) extract | 10.0% |
| 2 | *Prunus* (ethyl acetate) extract | 7.5% |
| 3 | Phospholipid | 2.5% |
| 4 | Cholesterol | 0.75% |
| 5 | Cream base (oil-in-water) | q.s. |

Example 5

| Sr. No. | Ingredient | Percentage |
| --- | --- | --- |
| 1 | *Ziziphus* alc. extract | 0.04% |
| 2 | *Prunus* aq. extract | 0.02% |
| 3 | Phospholipid | 0.86% |
| 4 | Cholesterol | 0.21% |
| 5 | Lotion base | q.s. |

Example 6

| Sr. No. | Ingredient | Percentage |
| --- | --- | --- |
| 1 | *Ziziphus* alc. extract | 0.05% |
| 2 | *Prunus* aq. extract | 0.03% |
| 3 | Phospholipid | 0.84% |
| 4 | Cholesterol | 0.21% |
| 5 | Gel base | q.s. |

Example 7

| Sr. No. | Ingredient | Percentage |
| --- | --- | --- |
| 1 | *Ziziphus* (ether) extract | 0.1% |
| 2 | *Prunus* alc. extract | 0.06% |
| 3 | Phospholipid | 1.25% |
| 4 | Cholesterol | 0.21% |
| 5 | Ointment base | q.s. |

Example 8

| Sr. No. | Ingredient | Percentage |
| --- | --- | --- |
| 1 | *Ziziphus* alc. Extract | 2.0% |
| 2 | *Prunus* aq. Extract | 1.2% |
| 3 | Phospholipid | 1.05% |
| 4 | Cholesterol | 0.21% |
| 5 | Powder base | q.s. |

The formulations were tested for safety and efficacy. In vitro studies were carried out on cell lines (fibroblast cell lines). Results were compared against commercially available samples and formats without delivery system. In vivo studies were also carried out on human volunteers. The study was a test under dermatological control, randomized, double blind, controlled and comparative versus initial state and each other.

Results of one of the preferred embodiments are shown below to demonstrate the synergistic action.

SUMMARY OF ANTI-WRINKLE EVALUATION
PAIRED t TEST of DIFFERENCE AT 30, 60 & 90 DAYS FOR EACH PRODUCT
Versus Initial State
(Jin-Ho-Chung Scale)

| Treatment | Parameter | N | Minimum | Maximum | Average | SD | CV | TValue | PValue |
| --- | --- | --- | --- | --- | --- | --- | --- | --- | --- |
| A | DIFF at THIRTY | 11 | 0 | 2 | 1.00000 | 0.89443 | 89.443 | 3.70810 | 0.00405 |
| A | DIFF at SIXTY | 11 | 0 | 3 | 1.63636 | 0.92442 | 56.492 | 5.87095 | 0.00016 |
| A | DIFF at NINETY | 11 | 1 | 4 | 1.90909 | 0.94388 | 49.441 | 6.70820 | 0.00005 |
| B | DIFF at THIRTY | 11 | 0 | 2 | 0.54545 | 0.82020 | 150.370 | 2.20564 | 0.05194 |
| B | DIFF at SIXTY | 11 | 0 | 4 | 1.63636 | 1.36182 | 83.222 | 3.98527 | 0.00258 |
| B | DIFF at NINETY | 11 | 0 | 4 | 1.72727 | 1.48936 | 86.226 | 3.84644 | 0.00323 |

SUMMARY OF ANTI-WRINKLE EVALUATION
PAIRED t TEST of DIFFERENCE AT 30, 60 & 90 DAYS FOR EACH PRODUCT
Versus Initial State
(Investigator Global Scale)

| Treatment | Parameter | N | Minimum | Maximum | Average | SD | CV | TValue | PValue |
| --- | --- | --- | --- | --- | --- | --- | --- | --- | --- |
| A | DIFF INV at THIRTY | 11 | 0 | 4 | 2.00000 | 1.84391 | 92.195 | 3.59738 | 0.00487 |
| A | DIFF INV at SIXTY | 11 | 0 | 6 | 3.18182 | 1.99089 | 62.571 | 5.30060 | 0.00035 |
| A | DIFF INV at NINETY | 11 | 2 | 8 | 4.72727 | 2.10195 | 44.464 | 7.45908 | 0.00002 |
| B | DIFF INV at THIRTY | 11 | −2 | 4 | 0.54545 | 2.01810 | 369.985 | 0.89642 | 0.39110 |
| B | DIFF INV at SIXTY | 11 | −2 | 8 | 3.00000 | 2.68328 | 89.443 | 3.70810 | 0.00405 |
| B | DIFF INV at NINETY | 11 | 0 | 8 | 4.09091 | 2.73695 | 66.903 | 4.95734 | 0.00057 |

A - Refers to one of the preferred embodiments
B - Conventional formulation

'p' value < 0.05 indicates that the results are statistically significant at 95% confidence level. Lower the 'p' value, greater the significance.

Combinations of the herbal extracts with delivery system showed statistically significant improvement vis-à-vis initial state and faster onset of efficacy, thereby demonstrating faster/better absorption of bio-actives vis-à-vis formulations without delivery system.

It is to be noted that the present invention is susceptible to modifications, adaptations and changes by those skilled in the art. Such variant embodiments employing the concepts and features of this invention are intended to be within the scope of the present invention, which is further set forth under the following claims.

We claim:

1. A polyherbal composition effective in skin care, comprising:
   a. 0.01% to 15% of an ethanolic *Ziziphus mauritanana* extract;
   b. 0.01% to 10% of an aqueous *Prunus puddum* extract;
   c. a delivery system comprising a lipid nanoparticle; and
   d. a carrier.

2. The polyherbal composition effective in skin care as claimed in claim 1, wherein the carrier is a dermatologically acceptable carrier.

3. The polyherbal composition effective in skin care as claimed in claim 1, wherein the delivery system comprises:
   a. at least one phospholipid; and
   b. at least one sterol.

4. The polyherbal composition effective in skin care as claimed in claim 1, wherein the composition provides anti-aging benefits.

5. The polyherbal composition effective in skin care as claimed in claim 1, wherein the composition provides anti-wrinkle benefits.

6. The polyherbal composition effective in skin care as claimed in claim 1, wherein the composition provides skin lightening benefits.

7. A method of treating skin comprising topically administering an effective amount of a polyherbal composition comprising:
   0.01% to 15% of an ethanolic *Ziziphus mauritanana* extract;
   0.01% to 15% of an aqueous *Prunus puddum* extract;
   a delivery system comprising a lipid nanoparticle; and
   a carrier.

8. The method of claim 7, wherein the delivery system comprises:
   at least one phospholipid; and
   at least one sterol.

9. The polyherbal composition of claim 1, wherein the composition comprises:
   a. 0.04% to 10% of an ethanolic *Ziziphus mauritanana* extract;
   b. 0.02% to 7.5% of an aqueous *Prunus puddum* extract;
   c. a delivery system comprising a lipid nanoparticle;
   d. a carrier; and
   e. a preservative.

* * * * *

UNITED STATES PATENT AND TRADEMARK OFFICE
CERTIFICATE OF CORRECTION

PATENT NO. : 9,572,766 B2  
APPLICATION NO. : 14/371106  
DATED : February 21, 2017  
INVENTOR(S) : Sukhjeet Kaur Gujral et al.

Page 1 of 1

It is certified that error appears in the above-identified patent and that said Letters Patent is hereby corrected as shown below:

On the Title Page

Column 2, OTHER PUBLICATIONS, Line 1, delete "Merrriam" and insert -- Merriam --

In the Claims

Column 7, Line 15, Claim 1, delete "mauritanana" and insert -- mauritiana --

Column 8, Line 10, Claim 7, delete "mauritanana" and insert -- mauritiana --

Column 8, Line 22, Claim 9, delete "mauritanana" and insert -- mauritiana --

Signed and Sealed this  
Second Day of May, 2017

Michelle K. Lee  
*Director of the United States Patent and Trademark Office*